US012766000B2

(12) United States Patent
Genovese et al.

(10) Patent No.: US 12,766,000 B2
(45) Date of Patent: Oct. 20, 2026

(54) HEART VALVE REPAIR

(71) Applicant: Medtronic Vascular, Inc., Santa Rosa, CA (US)

(72) Inventors: Matthew E. Genovese, Windsor, CA (US); Vania Lee, Circle Pines, MN (US); Russell Pribanic, Roxbury, CT (US); Thomas J. McPeak, Caledonia, MN (US); Jeffrey Sandstrom, Scandia, MN (US); Dermot O'Brien, Ballinasloe (IE); James Calvin Allan, Boise, ID (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1200 days.

(21) Appl. No.: 17/635,274

(22) PCT Filed: Aug. 4, 2020

(86) PCT No.: PCT/US2020/044809
§ 371 (c)(1),
(2) Date: Feb. 14, 2022

(87) PCT Pub. No.: WO2021/034497
PCT Pub. Date: Feb. 25, 2021

(65) Prior Publication Data

US 2022/0287839 A1 Sep. 15, 2022

Related U.S. Application Data

(60) Provisional application No. 62/888,212, filed on Aug. 16, 2019.

(51) Int. Cl.
*A61F 2/24* (2006.01)
*A61B 17/04* (2006.01)

(52) U.S. Cl.
CPC .......... *A61F 2/2466* (2013.01); *A61F 2/2454* (2013.01); *A61B 17/0469* (2013.01);
(Continued)

(58) Field of Classification Search
CPC ......... A61B 17/083; A61B 2017/00584; A61F 2/2427; A61F 2/2445; A61F 2/2454; A61F 2/2457; A61F 2/2466
See application file for complete search history.

(56) References Cited

U.S. PATENT DOCUMENTS 6,165,183 A 12/2000 Kuehn et al.
6,269,819 B1 8/2001 Oz et al.
(Continued)

FOREIGN PATENT DOCUMENTS

EP 1674040 A2 6/2006
WO 2018156640 A1 8/2018
WO 2018178977 A1 10/2018

OTHER PUBLICATIONS

First Office Action and Search Report from counterpart Chinese Application No. 202080057646.7 dated Mar. 7, 2025, 11 pp. Translation Attached.
(Continued)

*Primary Examiner* — Sarah W Aleman
(74) *Attorney, Agent, or Firm* — Shumaker & Sieffert, P.A.

(57) ABSTRACT

A medical system includes a catheter navigable through vasculature of patient to introduce a valve clip configured to join the edges of heart valve leaflets. The valve clip includes a deformable wire configured to engage valve leaflets, the wire extending from a first wire portion to a second wire portion. The catheter includes a handle having control members, an elongate body defining a lumen extending from the handle to a distal opening, and first and second delivery
(Continued)

devices operatively coupled to a control member and extending through the lumen to the distal opening. Each delivery device is configured to releasably couple to a portion of the wire and moveable relative to the distal opening. The delivery devices are controllable at the handle to move the valve clip between an extended configuration and a contracted configuration to engage the valve leaflets.

20 Claims, 11 Drawing Sheets

(52) U.S. Cl.
CPC ................. *A61F 2210/0014* (2013.01); *A61F 2220/0016* (2013.01)

(56) References Cited

U.S. PATENT DOCUMENTS 6,312,447 B1 11/2001 Grimes
6,419,696 B1 7/2002 Ortiz et al.
6,461,366 B1 10/2002 Seguin
6,575,971 B2 6/2003 Hauck et al.
6,626,930 B1 9/2003 Allen et al.
6,629,534 B1 10/2003 Goar et al.
6,695,866 B1 2/2004 Kuehn et al.
6,719,767 B1 4/2004 Kimblad
6,730,121 B2 * 5/2004 Ortiz .................... A61F 2/2466 623/2.37
6,743,239 B1 6/2004 Kuehn et al.
6,752,813 B2 6/2004 Goldfarb et al.
6,770,083 B2 8/2004 Seguin
6,840,246 B2 1/2005 Downing
6,875,224 B2 4/2005 Grimes
6,926,715 B1 8/2005 Hauck et al.
6,926,730 B1 8/2005 Nguyen et al.
6,978,176 B2 12/2005 Lattouf
7,011,669 B2 3/2006 Kimblad
7,083,628 B2 8/2006 Bachman
7,094,244 B2 8/2006 Schreck
7,112,207 B2 9/2006 Allen et al.
7,160,299 B2 1/2007 Baily
7,226,467 B2 6/2007 Lucatero et al.
7,288,097 B2 10/2007 Seguin
7,373,207 B2 5/2008 Lattouf
7,381,210 B2 6/2008 Zarbatany et al.
7,464,712 B2 12/2008 Oz et al.
7,509,959 B2 3/2009 Oz et al.
7,513,908 B2 4/2009 Lattouf
7,534,260 B2 5/2009 Lattouf
7,559,936 B2 7/2009 Levine
7,563,267 B2 7/2009 Goldfarb et al.
7,563,273 B2 7/2009 Goldfarb et al.
7,569,062 B1 8/2009 Kuehn et al.
7,604,646 B2 10/2009 Goldfarb et al.
7,608,091 B2 10/2009 Goldfarb et al.
7,628,797 B2 12/2009 Tieu et al.
7,635,329 B2 12/2009 Goldfarb et al.
7,655,015 B2 2/2010 Goldfarb et al.
7,682,369 B2 3/2010 Seguin
7,736,388 B2 6/2010 Goldfarb et al.
7,744,609 B2 6/2010 Allen et al.
7,744,611 B2 6/2010 Nguyen et al.
7,753,923 B2 7/2010 St. Goar et al.
7,758,595 B2 7/2010 Allen et al.
7,758,596 B2 7/2010 Oz et al.
7,780,700 B2 8/2010 Frazier et al.
7,803,187 B2 9/2010 Hauser
7,811,296 B2 10/2010 Goldfarb et al.
7,871,433 B2 1/2011 Lattouf
7,887,552 B2 2/2011 Bachman
7,914,544 B2 3/2011 Nguyen et al.
7,938,827 B2 5/2011 Hauck et al.
7,981,123 B2 7/2011 Seguin
7,998,151 B2 8/2011 St. Goar et al.
8,029,565 B2 10/2011 Lattouf
8,052,592 B2 11/2011 Goldfarb et al.
8,057,493 B2 11/2011 Goldfarb et al.
8,062,313 B2 11/2011 Kimblad
8,070,746 B2 12/2011 Orton et al.
8,133,239 B2 3/2012 Oz et al.
8,172,856 B2 5/2012 Eigler et al.
8,187,299 B2 5/2012 Goldfarb et al.
8,216,230 B2 7/2012 Hauck et al.
8,216,256 B2 7/2012 Raschdorf, Jr. et al.
8,241,304 B2 8/2012 Bachman
8,303,608 B2 11/2012 Goldfarb et al.
8,343,174 B2 1/2013 Goldfarb et al.
8,361,086 B2 1/2013 Allen et al.
8,409,273 B2 4/2013 Thornton et al.
8,425,504 B2 4/2013 Orton et al.
8,470,028 B2 6/2013 Thornton et al.
8,475,472 B2 7/2013 Bachman
8,500,761 B2 8/2013 Goldfarb et al.
8,721,665 B2 5/2014 Oz et al.
8,734,505 B2 5/2014 Goldfarb et al.
8,740,918 B2 6/2014 Seguin
8,740,920 B2 6/2014 Goldfarb et al.
8,753,373 B2 6/2014 Chau et al.
8,771,292 B2 7/2014 Allen et al.
8,795,352 B2 8/2014 O'Beirnne et al.
8,945,177 B2 2/2015 Dell et al.
8,968,393 B2 3/2015 Rothstein
8,998,933 B2 4/2015 Rothstein et al.
9,011,468 B2 4/2015 Ketai et al.
9,044,246 B2 6/2015 Goldfarb et al.
9,060,858 B2 6/2015 Thornton et al.
9,192,374 B2 11/2015 Zentgraf
9,282,964 B1 3/2016 Cohen et al.
9,314,242 B2 4/2016 Bachman
9,364,326 B2 6/2016 Yaron
9,427,237 B2 8/2016 Oz et al.
9,504,570 B2 11/2016 Hauser et al.
9,510,829 B2 12/2016 Goldfarb et al.
9,510,837 B2 12/2016 Seguin
9,572,666 B2 2/2017 Basude et al.
9,629,716 B2 4/2017 Seguin
9,649,106 B2 5/2017 Nobles et al.
9,700,412 B2 7/2017 Yaron et al.
10,080,660 B2 * 9/2018 Keane .................. A61F 2/2454
2001/0005787 A1 6/2001 Oz et al.
2003/0120340 A1 6/2003 Liska et al.
2003/0120341 A1 6/2003 Shennib et al.
2004/0024414 A1 2/2004 Downing
2004/0039442 A1 2/2004 St. Goar et al.
2004/0162610 A1 8/2004 Liska et al.
2004/0243227 A1 12/2004 Starksen et al.
2005/0033446 A1 2/2005 Deem et al.
2005/0149014 A1 7/2005 Hauck et al.
2005/0159810 A1 7/2005 Filsoufi
2005/0267529 A1 12/2005 Crockett et al.
2006/0229708 A1 10/2006 Powell et al.
2006/0293698 A1 12/2006 Douk
2007/0038293 A1 2/2007 St. Goar et al.
2007/0061010 A1 3/2007 Hauser et al.
2007/0100356 A1 5/2007 Lucatero et al.
2007/0118151 A1 5/2007 Davidson
2007/0129737 A1 6/2007 Goldfarb et al.
2007/0198038 A1 8/2007 Cohen et al.
2007/0255396 A1 11/2007 Douk et al.
2007/0265702 A1 11/2007 Lattouf
2008/0167714 A1 7/2008 St. Goar et al.
2008/0183283 A1 7/2008 Downing
2008/0228201 A1 9/2008 Zarbatany et al.
2008/0319541 A1 12/2008 Filsoufi
2009/0118744 A1 5/2009 Wells et al.
2009/0177266 A1 7/2009 Powell et al.
2009/0222026 A1 9/2009 Rothstein et al.
2010/0137887 A1 6/2010 Crockett et al.
2010/0217283 A1 8/2010 St. Goar et al.
2010/0262167 A1 10/2010 Jelich et al.
2010/0298929 A1 11/2010 Thornton et al.
2010/0318184 A1 12/2010 Spence

(56) References Cited

U.S. PATENT DOCUMENTS

| | | | |
|---|---|---|---|
| 2011/0015722 | A1 | 1/2011 | Hauser et al. |
| 2011/0060407 | A1 | 3/2011 | Ketai et al. |
| 2011/0092988 | A1 | 4/2011 | Cohen et al. |
| 2011/0093063 | A1 | 4/2011 | Schreck |
| 2011/0144743 | A1 | 6/2011 | Lattouf |
| 2011/0213387 | A1 | 9/2011 | Nguyen et al. |
| 2012/0010461 | A1 | 1/2012 | Goldfarb et al. |
| 2012/0065464 | A1 | 3/2012 | Ellis et al. |
| 2012/0158020 | A1 | 6/2012 | Crockett et al. |
| 2012/0209376 | A1 | 8/2012 | Hauser et al. |
| 2012/0277853 | A1 | 11/2012 | Rothstein |
| 2012/0310331 | A1 | 12/2012 | Eigler et al. |
| 2013/0253641 | A1 | 9/2013 | Attouf |
| 2013/0282059 | A1 | 10/2013 | Ketai et al. |
| 2014/0066693 | A1 | 3/2014 | Goldfarb et al. |
| 2014/0207161 | A1 | 7/2014 | Dell et al. |
| 2014/0228871 | A1 | 8/2014 | Coben et al. |
| 2014/0379074 | A1* | 12/2014 | Spence ................. A61F 2/2466 623/2.11 |
| 2015/0105804 | A1 | 4/2015 | Dell et al. |
| 2015/0182223 | A1 | 7/2015 | Keta et al. |
| 2015/0223793 | A1 | 8/2015 | Goldfarb et al. |
| 2016/0113762 | A1 | 4/2016 | Clague et al. |
| 2016/0174979 | A1 | 6/2016 | Wei |
| 2016/0192925 | A1 | 7/2016 | Bachman |
| 2016/0242909 | A1 | 8/2016 | Ketai et al. |
| 2016/0287387 | A1 | 10/2016 | Wei |
| 2016/0354082 | A1 | 12/2016 | Oz et al. |
| 2017/0020521 | A1 | 1/2017 | Krone et al. |
| 2017/0042546 | A1 | 2/2017 | Goldfarb et al. |
| 2017/0049455 | A1 | 2/2017 | Seguin |
| 2017/0143330 | A1 | 5/2017 | Basude et al. |
| 2017/0354500 | A1 | 12/2017 | Martinez et al. |
| 2018/0055628 | A1* | 3/2018 | Patel ..................... A61F 2/2427 |
| 2018/0250127 | A1 | 9/2018 | Maimon et al. |
| 2018/0360605 | A1 | 12/2018 | Zerkowski et al. |

OTHER PUBLICATIONS

Feldman et al., "Percutaneous Approaches to Valve Repair for Mitral Regurgitation", Journal of the American College of Cardiology, vol. 63, No. 20, Elsevier Inc., May 27, 2014, pp. 2057-2068.

International Search Report and Written Opinion of International Application No. PCT/US2020/044809 dated Oct. 28, 2020, 11 pp.

* cited by examiner

HEART VALVE REPAIR

The present application is a U.S. national stage filing under 35 U.S.C. § 371 of International Application No. PCT/US2020/044809, filed Aug. 4, 2020, and entitled, "HEART VALVE REPAIR," which claims the benefit of U.S. Provisional Application No. 62/888,212,filed Aug. 16, 2019, and entitled, "HEART VALVE REPAIR," the entire content of each of which is incorporated herein by reference.

TECHNICAL FIELD

This disclosure relates to heart valve repair, such as mitral valve repair.

BACKGROUND

Some patient conditions can produce valvular insufficiency or regurgitation in a heart of the patient. Valvular insufficiency or regurgitation occurs when a valve in a heart of a patient does not close completely, allowing blood to flow backwards (e.g., from the left ventricle to the left atrium), which may adversely impact the functionality of the heart.

The mitral valve includes two leaflets (anterior and posterior) attached to an annulus (e.g., a fibrous ring). In a healthy heart, the mitral valve leaflets close during contraction of the left ventricle and prevent blood from flowing back into the left atrium. Mitral valve regurgitation is a condition in which the leaflets of a mitral valve of a patient do not coapt properly and, as a result, blood regurgitates back into the left atrium from the left ventricle. The regurgitation of blood back into the left atrium may result in a reduced ejection volume from the left ventricle, causing the heart of the patient to work relatively harder to supply the desirable volume of blood to the body. Mitral regurgitation may occur because of different patient conditions. For example, secondary mitral regurgitation, also referred to as functional mitral regurgitation, may occur when a left ventricle dilates and causes dilation of the mitral annulus of a patient.

SUMMARY

The present disclosure describes medical devices, systems and techniques that can be used to help engage tissue, such as leaflets of a heart valve, in order to implant a valve clip configured to treat valve regurgitation. The devices, systems, and techniques described herein may be used to treat mitral valve regurgitation or other patient conditions that involve valves. In some examples, the devices, systems, and technique may include transcatheter repair solutions for degenerative mitral regurgitation.

In some examples, this disclosure describes example medical systems including a valve clip including a deformable wire configured to engage valve leaflets of a patient, where the deformable wire extends from a first wire portion to a second wire portion; and a catheter configured to introduce the valve clip adjacent a native heart valve in a patient, the catheter including a handle including a plurality of control members; an elongate body defining a lumen, where the elongate body extends from a proximal end mechanically coupled to the handle to a distal portion including a distal opening; a first delivery device operatively coupled to at least one control member of the plurality of control members and extending through the lumen to the distal opening, where the first delivery device is configured to be releasably coupled to the first wire portion and moveable relative to the distal opening of the elongate body; and a second delivery device operatively coupled to at least one control member of the plurality of control members and extending through the lumen to the distal opening, where the second delivery device is configured to be releasably coupled to the second wire portion, where the first and second delivery device are configured to move the valve clip between an extended configuration and a contracted configuration to engage the valve leaflets.

In some examples, this disclosure describes example medical systems including a valve clip including a deformable wire extending from a distal fixation structure to a proximal fixation structure, where the deformable wire is moveable between an extended configuration and a preformed contracted configuration configured to engage valve leaflets; a plurality of barbs extending from an exterior surface of the wire; and a fabric positioned exterior to the plurality of barbs, where the plurality of barbs are configured to at least partially protrude through the fabric when the wire engages the valve leaflets; and a catheter configured to introduce the valve clip adjacent a native heart valve in a patient, the catheter including a handle including a plurality of control members; an elongate body defining a lumen, where the elongate body extends from a proximal end mechanically coupled to the handle to a distal opening; a first delivery device operatively coupled to at least one control member of the plurality of control members and extending through the lumen to the distal opening, where the first delivery device is configured to be releasably coupled to the distal fixation member of the deformable wire and movable relative to the distal opening of the elongate body; and a second delivery device of the plurality of delivery devices operatively coupled to at least one control member of the plurality of control members and extending through the lumen to the distal opening, where the second delivery device is configured to be releasably coupled to the proximal fixation member of the deformable wire, where the first and second delivery device are configured to pass the valve clip in the extended configuration through the distal opening of the elongate body and move the valve clip between the extended configuration and the contracted configuration to engage the valve leaflets.

In some examples, this disclosure describes example techniques that include advancing a catheter through vasculature of a patient to a vascular or cardiac selected tissue site, where the catheter includes a lumen housing a valve clip including a deformable wire configured to engage valve leaflets of a patient, where the deformable wire extends from a first wire portion to a second wire portion, and where the catheter further includes a handle including a plurality of control members; an elongate body defining the lumen, where the elongate body extends from a proximal end mechanically coupled to the handle to a distal portion including a distal opening; and a first delivery device operatively coupled to at least one control member of the plurality of control members and extending through the lumen to the distal opening, where the first delivery device is configured to be releasably coupled to the first wire portion and movable relative to the distal opening of the elongate body; and a second delivery device of the plurality of delivery devices operatively coupled to at least one control member of the plurality of control members and extending through the lumen to the distal opening, where the second delivery device is configured to be releasably coupled to the second wire portion; advancing the first delivery device distal to the distal opening of the elongate body; and controlling the first delivery device and the second delivery device to move the valve clip from an extended configuration to a contracted configuration to engage the valve leaflets.

The details of one or more examples are set forth in the accompanying drawings and the description below. Other features, objects, and advantages will be apparent from the description and drawings, and from the claims.

DETAILED DESCRIPTION

Figure 1A:
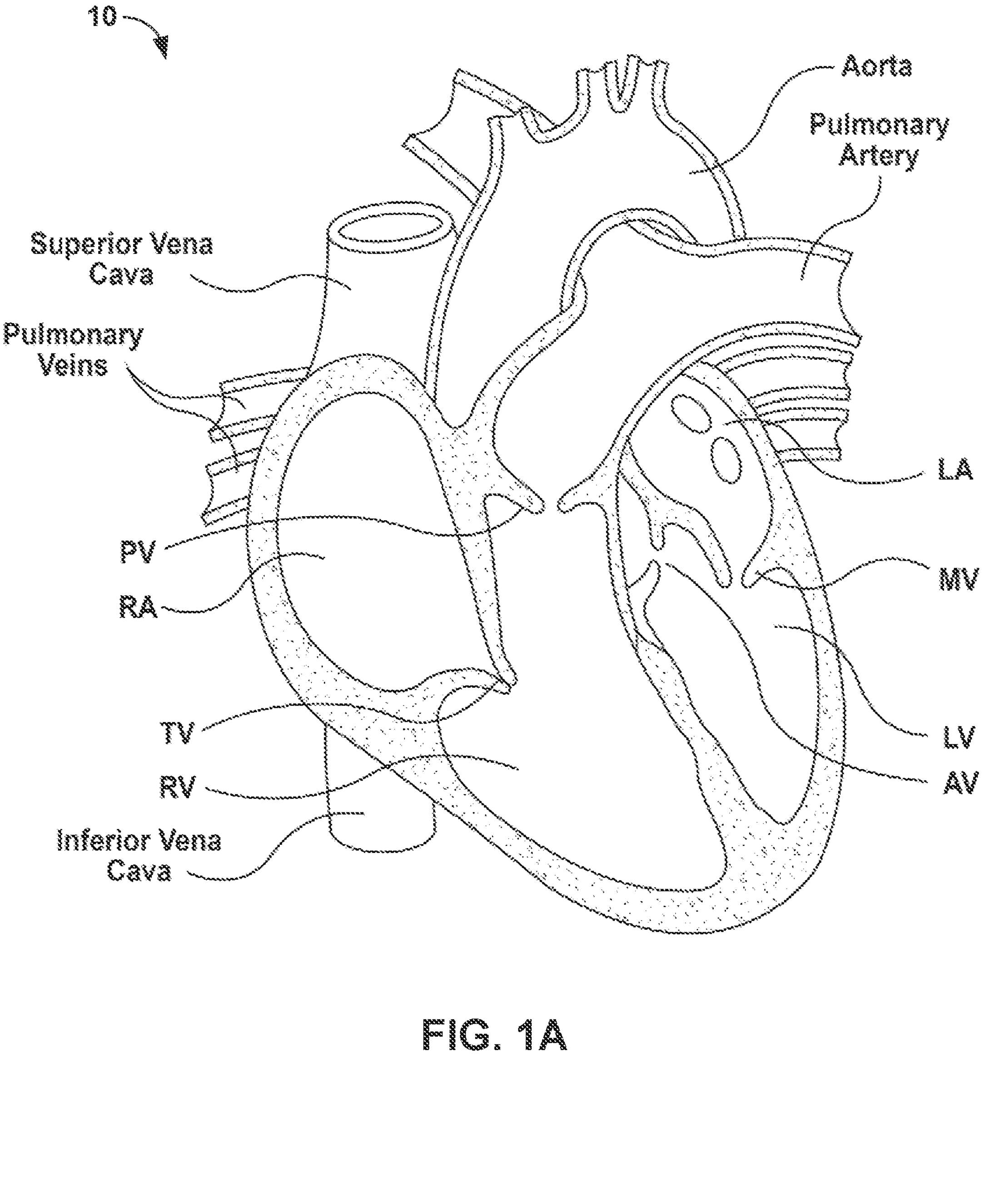
FIGS. 1A and 1B are schematic cross-sectional views of an example human heart.

This disclosure describes devices, systems, and techniques for repairing a heart valve, such as, but not limited to, a mitral valve, that are a less invasive compared to some other techniques, such as open heart surgeries. In some cases, a heart valve of a patient is repaired by clamping or suturing the leaflets of the heart valve together, effectively dividing the valve orifice into separate functioning orifices (e.g., two semilunar valves). This may be referred to as edge-to-edge valve repair.

The devices and systems described herein may be used as part of an edge-to-edge valve repair and may facilitate the performing of such a medical procedure via a transcatheter technique (e.g., eliminating the need for an open heart surgery or a more invasive technique). As discussed in further detail below, the devices and systems described herein are configured to facilitate grasping leaflets of a heart valve using a valve clip including a deformable spiral shape. The valve clip may be deformed into an extended configuration. In the extended configuration, the spiral shape of the valve clip may be straight or nearly straight to enable delivery of the valve clip through a lumen of a delivery catheter. The delivery catheter may be navigated through vasculature of a patient and positioned at or near a selected valve of the heart. When positioned at a selected location, e.g., within the plane of the valve, the valve clip may be deployed from the delivery catheter. The valve clip may be retracted to a preformed shape (e.g., an undeformed configuration). As the valve clip is manipulated from the deformed configuration to the undeformed configuration, the spiral clip may engage and capture the valve leaflets. In this way, the spiral clip is configured to clip together the leaflets.

In some examples, a plurality of valve clips may be used to clip together the leaflets. In some examples, the valve clip may enable the leaflets to be subsequently sutured, clamped (e.g., with a second clip), or otherwise connected at or near the edge of the leaflets. In other examples, the valve clip alone may be sufficient to clip together the leaflets. In some examples, grasping the leaflets simultaneously (e.g., at the same time or nearly at the same time) with the spiral clip may improve placement of the spiral clip and/or decrease the amount of time required to achieve the desired placement of the spiral clip with respect to the annulus of the heart valve and/or edges of the valve leaflets. In some examples, the disclosed devices, systems, and techniques may enable assessing functionality of the valve clip while still having the ability to reposition or retrieve the valve clip. Assessing functionally of the valve clip while still being able to reposition or retrieve the valve clip may improve effectiveness of the treatment.

Edge-to-edge heart valve repair may be useful for treating heart valve regurgitation, e.g., for patients with relatively normal leaflet motion (compared to a healthy heart that does not have degenerative mitral regurgitation) and/or with a dilated annulus or leaflet prolapse. Leaflet prolapse may be due to chordal rupture or papillary muscle elongation. While some regurgitation may persist after an edge-to-edge heart valve repair, the edge-to-edge heart valve repair may be sufficient to reduce the regurgitation enough to slow or even halt further progression into heart failure.

Figure 1B:
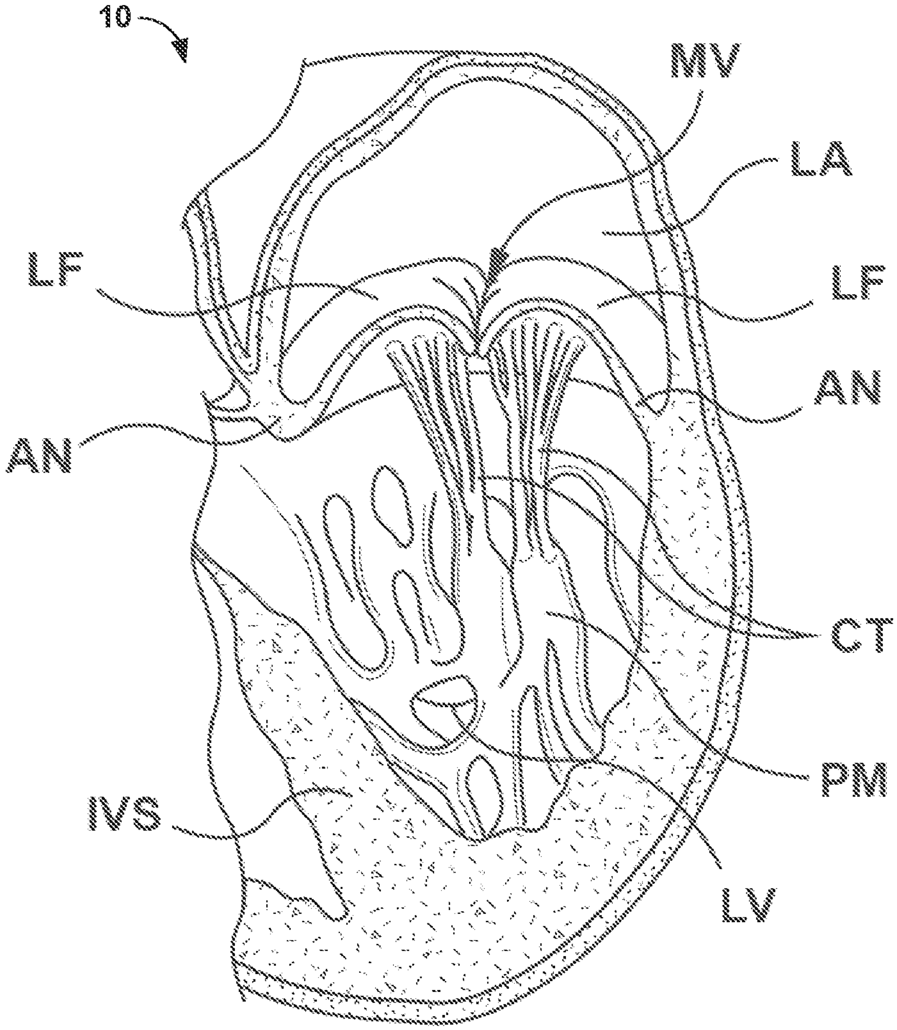

FIGS. 1A and 1B are schematic cross-sectional views of an example human heart 10. The human heart 10 is a four-chambered, muscular organ that provides blood circulation through the body during a cardiac cycle. The four chambers include the right atrium (RA) and right ventricle (RV) which supply the pulmonary circulation, and the left atrium (LA) and left ventricle (LV) which supply oxygenated blood received from the lungs to the body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body, respectively. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or coapt to close and prevent backflow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendineae (CT).

Mitral valve regurgitation is a condition in which the leaflets of a mitral valve of a patient do not coapt properly. As a result, blood regurgitates back into the left atrium LA from the left ventricle LV. The regurgitation of blood back into the left atrium LA may result in a reduced ejection volume from the left ventricle LV, causing the heart of the patient to work relatively hard to supply the desirable volume of blood to the body. Mitral regurgitation may occur because of one or more patient conditions. For example, secondary mitral regurgitation, also referred to as functional mitral regurgitation, may occur when the left ventricle LV dilates and causes dilation of the mitral annulus of a patient. The leaflets LF of the valves may move apart as a result of the dilation of the left ventricle LV, which may adversely impact the ability of the leaflets to properly coapt.

In addition to or instead of being caused by dilation of the left ventricle LV, mitral valve regurgitation (or other valve regurgitation) may be caused by calcified plaque buildup in heart 10. For example, the leaflets LF of the valves (e.g., aortic valve AV or mitral valve MV) may harden and may not sufficiently coapt, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated.

The medical devices, systems, and techniques described herein may be used to repair a valve of heart 10 via a minimally invasive medical procedure. For example, the medical procedure may include delivery of a valve clip via a transcatheter, trans-septal or left ventricle approach that is less invasive than open heart surgery. While open heart surgeries, such as annuloplasty preformed via open heart surgery, may have positive outcomes, a more minimally invasive medical procedure may also be associated with positive outcomes, as well as a shorter recovery time for some patients compared to open heart surgery. While the devices, systems, and techniques are primarily described herein with reference to repair of the mitral valve MV, in other examples, the devices, systems, and techniques described herein can be used to repair other heart valves or other valves outside of the heart of a patient. Additionally, the devices, systems, and techniques may be used with other medical devices or medical procedures such as with an annuloplasty ring that goes around the annulus of the mitral valve MV for annulus stability.

Figure 2A:
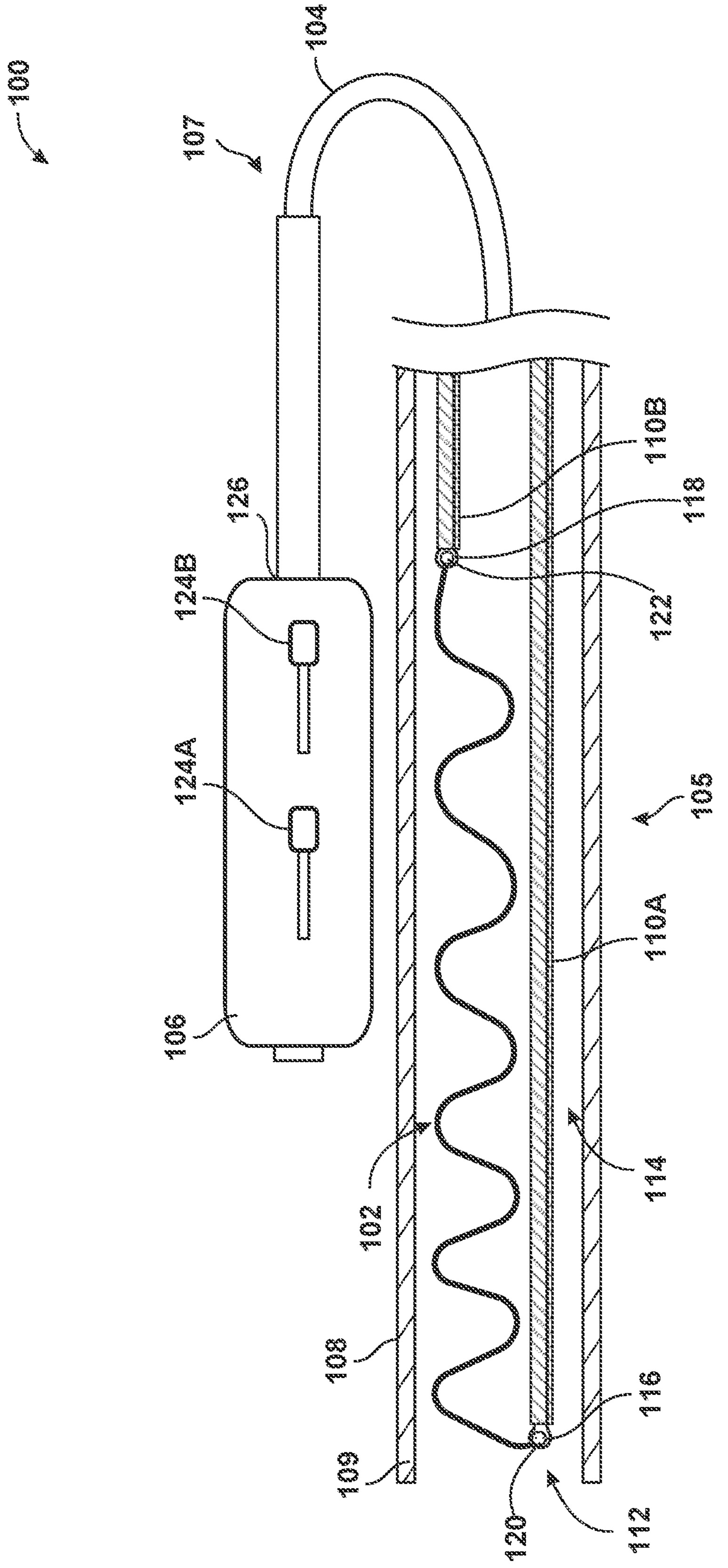
FIG. 2A-2D are schematic diagrams illustrating an example medical system and technique of introducing a valve clip to a selected tissue site.

FIG. 2A-2D are schematic diagrams illustrating an example medical system 100 and technique of introducing a valve clip 102 to a selected tissue site. FIG. 2A is a schematic diagram illustrating a partial cut-away section of an example medical system 100 including a catheter 104 and a valve clip 102. Catheter 104 includes a handle 106, an elongate body 108, a first delivery device 110A, and a second delivery device 110B. For purposes of illustration, a distal portion 105 of catheter 104 is enlarged relative to handle 106 and a proximal portion 107 of catheter 104. In actuality, an outer diameter of distal portion 105 may be substantially similar to an outer diameter of proximal portion 107.

Valve clip 102 includes a deformable wire configured to engage a tissue of a patient, such as leaflets LF of a heart valve. Valve clip 102 may include a biocompatible material that is configured to apply or maintain a force on a tissue. For example, valve clip 102 may be configured to apply a force to leaflets LF to join at least a portion of leaflets LF or urge at least a portion of leaflets LF toward each other to improve coaptation of leaflets LF. In some examples, valve clip 102 may include a biocompatible metal or alloy, such as nitinol, stainless steel, a cobalt-chromium alloy, or the like. In other examples, valve clip 102 may include a polymer, a suture, a composite, or any combination of suitable materials. For example, valve clip 102 may consist essentially of a metal or alloy. In some instances, valve clip 102 may include a biocompatible shape memory alloy. In addition to or instead of a metal or alloy, in some examples, valve clip 102 may include a polymer. For example, valve clip 102 may consist essentially of a polymer or may be formed from a composite of metal or polymer. As another example, valve clip 102 may be formed from poly-paraphenylene terephthalamide (e.g., Kevlar, DuPont, Wilmington, Delaware).

In some examples, valve clip 102 may have a contracted (e.g., undeformed) configuration defining a preformed shape. For example, the preformed shape may be defined or set using a heat treatment. The preformed shape is a shape toward which valve clip 102 recovers in the absence of an applied force. In some examples, the preformed shape may include a substantially planar spiral (e.g., planar within manufacturing tolerances), a helix, a conical spiral, or other spring-like shape. The preformed shape is configured to cause valve clip 102 to engage a tissue. In some examples, the preformed shape may cause valve clip 102 to engage a tissue by the capstan effect. For example, when valve clip 102 is engaged with a tissue, the preformed shape may cause the tissue to conform to a cross sectional shape of valve clip 102, thereby resulting in a friction force between the tissue and valve clip 102. In some examples, tissue engagement may result from or be increased with other features of valve clip 102, such as anchors, as discussed below.

Valve clip 102 is also deformable from the preformed shape. For example, an applied force may urge the preformed shape toward an extended (e.g., deformed) configuration. In the extended configuration valve clip 102 may be configured to pass through lumen 114 and/or distal opening 112 of elongate body 108. In this way, deforming valve clip 102 into the extended configuration may enable loading of valve clip 102 into catheter 104 for delivery to a selected tissue site. In some examples, the preformed shape (e.g., the contracted configuration) of valve clip 102 may have at least one dimension, e.g., width or height, greater than a cross-section of lumen 114 and/or distal opening 112.

Valve clip 102 extends from a distal end 116 to a proximal end 118. In some examples, distal end 116 and/or proximal end 118 may include a respective fixation structure 120 and/or 122. Fixation structures 120 and 122 are configured to releasably engage first delivery device 110A and second delivery device 110B, respectively, as discussed in further detail below. For example, fixation structures 120 and 122 may include a loop in the wire of valve clip 102, a hook, a bulbous structure, such as a ball, or the like.

In some examples, valve clip 102 may include at least one anchor. The anchors may include any structure configured to engage valve clip 102 to tissue at the selected tissue site, such as to leaflets LF, and help retain valve clip 102 substantially in place relative to the selected tissue site. For example, the anchors may be configured to penetrate at least a portion of the tissue at the selected tissue site, increase a coefficient of friction (e.g., improve a capstan effect) at the selected tissue site, and/or promote tissue ingrowth. The anchors may be positioned at one or more selected locations along a length of valve clip 102 and extend from or cover an exterior surface of the wire of valve clip 102. In some examples, the anchors may include a fabric, one or more barbs, one or more hooks, one or more helical coils, or one or more conical helical coils. In some examples, the anchors may include a biocompatible metal or alloy, such as nitinol, stainless steel, a cobalt-chromium alloy, or the like. In some instances, the anchors may include a biocompatible shape memory alloy. In addition to or instead of a metal, in some examples, the anchors may be formed at least partially from a polymer. For example, the anchor may include a biocompatible polymeric fabric, such as Dacron or the like. In some examples, the anchors may be fluorogenic, echogenic, or both.

Catheter 104 is configured to introduce valve clip 102 in a patient at a selected tissue site, such as mitral valve MV. Catheter 104 includes handle 106, elongate body 108, first delivery device 110A, and second delivery device 110B ("delivery devices 110").

Handle 106 may be configured to control movement of catheter 104 and/or deployment of valve clip 102. Handle 106 includes first control member 124A and second control member 124B ("control members 124"). Control members 124 may include any suitable device manipulatable by a clinician, such as, for example, a push button, a sliding lever, a dial, or the like. Control members 124 may be operatively coupled, such as mechanically coupled or fluidly coupled, to enable control of other components of catheter 104, such as delivery devices 110.

The clinician may position medical system 100 by advancing distal portion 105 of catheter 104 through vasculature of the patient, for example, from a femoral venous access site and up through the inferior vena cava IVC, or a radial artery access site. In some examples, to facilitate positioning of catheter 104, valve clip 102, or both, within the treatment location, a distal portion of catheter 104 may include at least one radiographic and/or echogenic marker configured to be visualized using a radiographic and/or ultrasound technique. In some examples, distal portion 105 of catheter 104 is configured to pierce a septum of the heart of a patient such that catheter 104 may access left atrium LA trans-septally. For example, trans-septal delivery of valve clip 102 to the mitral valve MV may include piercing the septum between the right atrium RA and left atrium LA. Delivery tool 106 may include articulating features to facilitate the navigation of distal portion 105 of catheter 104. For example, catheter 104 may include a pull wire assembly (not shown) integrated therein and being coupled to one of control members 124 that, when moved, causes distal portion 105 of catheter 104 to bend in a selected direction.

Elongate body 108 defines lumen 114 and extends from a proximal end 126 mechanically coupled to the handle 106 to a distal portion 105. Distal portion 105 defines distal opening 112 providing access to lumen 114. Distal opening 112 may be disposed at a distal end of distal portion, or extend through sidewall 109 of elongate member 108. Lumen 114 may be configured to house valve clip 102 during percutaneous introduction of catheter 104 into vasculature of a patient and advancing distal portion 105 to the selected tissue site. In some examples, lumen 114 may be configured for use with a guidewire, a guide catheter, or the like, to facilitate introducing catheter 104 into vasculature of a patient and advancing distal portion 105 of catheter 104 to the selected tissue site.

During use, valve clip 102 is loaded into catheter 104 for deployment to a selected tissue site (e.g. mitral valve MV). Valve clip 102 may be loaded through distal opening 112 of elongate body 108, or an opening in proximal portion 107 of catheter 104. In some examples, loading valve clip 102 may include releasably coupling valve clip 102 to delivery devices 110. For example, distal ends of first and second delivery devices 110A and 110B may include respective clamshell-shaped clamps 126A and 126B ("clamps 126"). In other examples, clamps 126 may include any suitable structure to releasably couple to at least a portion of valve clip 102. In some examples, clamps 126 may be controllable at control members 124 to engage or disengage clamps 126 with valve clip 102, such as a fixation members 120 and 122.

Catheter 104 is also configured to deploy valve clip 102 at a selected tissue site, e.g., mitral valve MV, to engage leaflets LF. For example, first delivery device 110A may be operatively coupled to control member 124A of the plurality of control members and extending through lumen 114 to distal opening 112. Similarly, second delivery device 110B may be operatively coupled to control member 124B and extending through lumen 114 to distal opening 112. First delivery device 110A is configured to be releasably coupled to a first wire portion of valve clip 102. In some examples, first delivery device 110A may be releasably coupled to fixation structure 120. Second delivery device 110B is configured to be releasably coupled to a second wire portion of valve clip 102. In some examples, second delivery device 110B may be releasably coupled to fixation structure 122. Delivery devices 110 are moveable relative to distal opening 112 of elongate body 104 to deploy valve clip 102 from lumen 114. For example, actuation of control members 124 that are operatively coupled to delivery device 110 may cause movement of delivery devices relative to distal opening 112. In this way, delivery device 110 may be used to move valve clip relative to distal opening 112 and between the extended configuration and the contracted configuration.

Figure 2B:
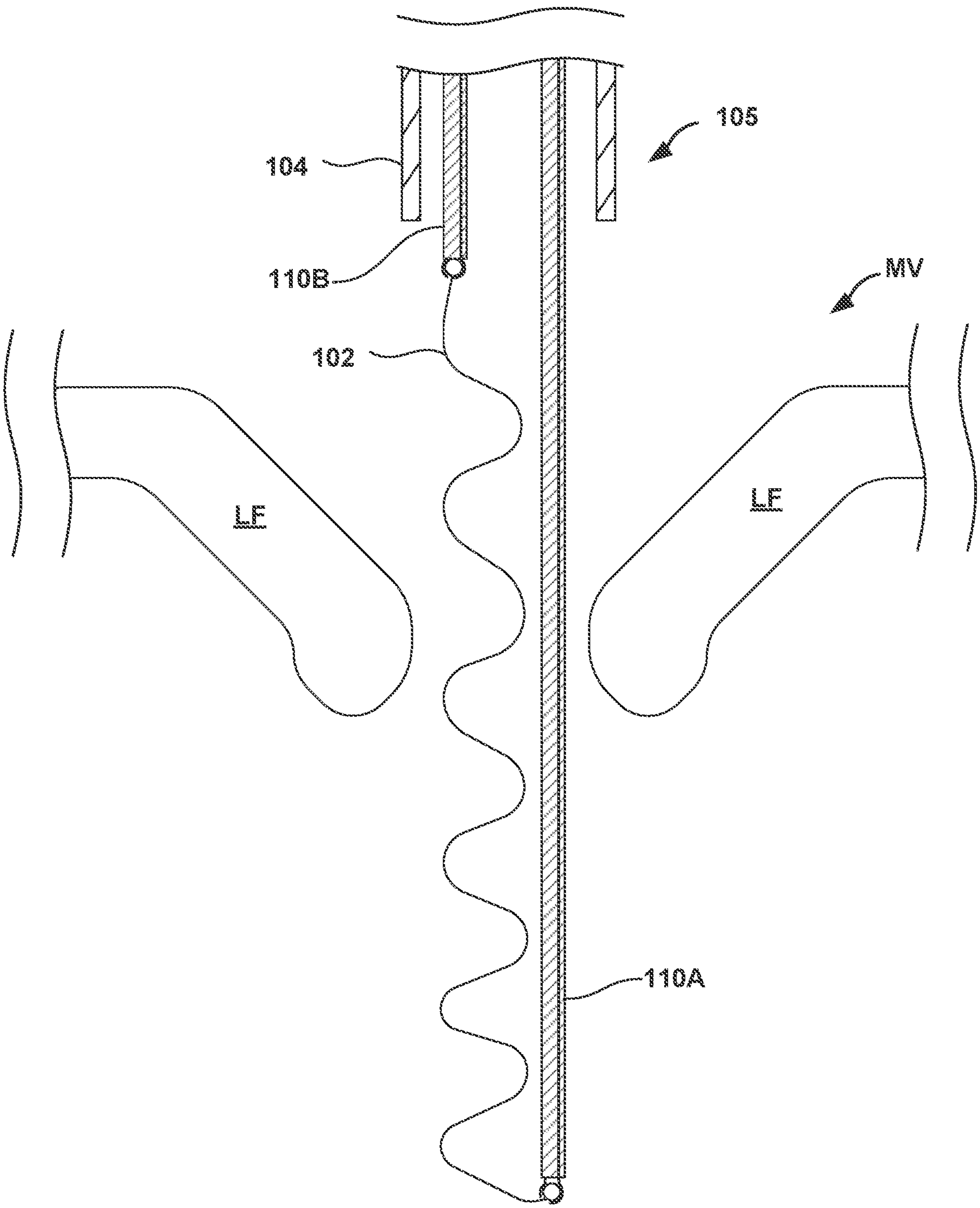

As illustrated in FIG. 2B, after positioning distal portion 105 of catheter 104 at a selected tissue site, e.g., adjacent a native heart valve in a patient, a clinician may actuate one or both of control members 124 to control the corresponding delivery device(s) 110 to deploy valve clip 102 out through distal opening 112. In some examples, during deployment, valve clip 102 may be in the extended configuration. When in the extended configuration, valve clip 102 is configured to pass through lumen 114 and distal opening 112 of elongate body 104.

Figure 2C:
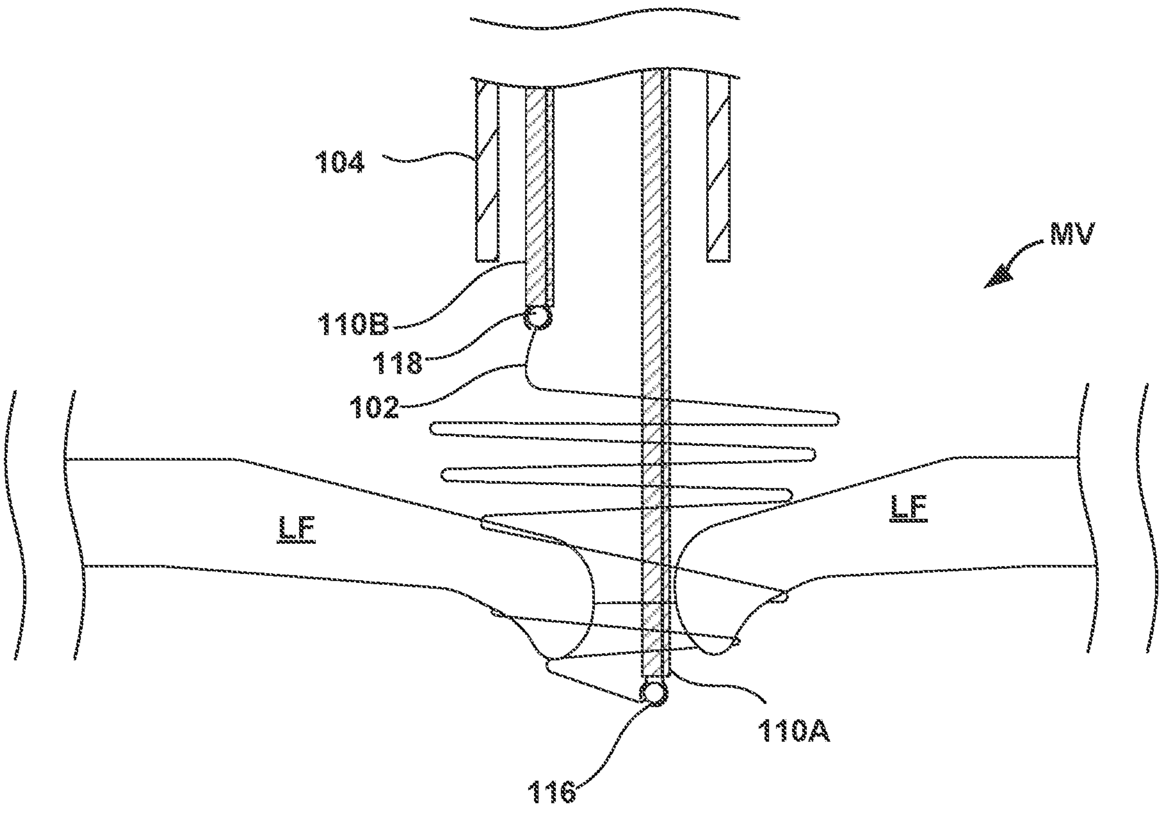

When deployed, valve clip 102 may be in the extended configuration and traverse mitral valve MV. After valve clip 102 in the extended configuration is positioned to traverse mitral valve MV, a clinician may manipulate one or both of control members 124 to control the corresponding delivery device(s) to move valve clip 102 between the extended configuration and the contracted configuration. For example, as illustrated in FIG. 2C, a clinician may actuate first control member 124A to move first delivery device 110A in a proximal direction, while not actuating to second control member 124B, which results in second delivery device 110B remaining stationary relative to distal opening 112 and/or mitral valve MV. In this way, the clinician may control distal end 116 of valve clip 102 to move toward proximal end 118 of valve clip 102 to return valve clip 102 toward the contracted configuration. In some examples, the clinician may actuate first control member 124A to move first delivery device 110A in a proximal direction, while actuating second control member 124B to move second delivery device 110B in a distal direction. In this way, the clinician may control distal end 116 of valve clip and proximal end 118 of valve clip 102 to move toward each other simultaneously to return valve clip 102 toward the contracted configuration. In some examples, the clinician may actuate second control member 124B to move second delivery device 110B in a distal direction, while the clinician does not actuate first control member 124A, which results in first delivery device 110A remaining stationary relative to distal opening 112 and/or mitral valve MV. In this way, the clinician may control proximal end 118 of valve clip 102 to move toward distal end 116 of valve clip 102 to return valve clip 102 toward the contracted configuration. After returning valve clip 102 to the contracted configuration, e.g., to the extend allowed when engaging leaflets LF, the clinician may actuate one or both control members 124 or another control element to release valve clip 102 from one or both delivery devices 110. In some examples, additionally or alternatively to actuating first and/or second control members 124A and 124B to move one or both delivery devices 110, the clinician may actuate one or both control members 124 or another control element to release valve clip 102 from one or both delivery devices 110 such that valve clip 102 returns toward the contracted configuration in an uncontrolled manner. For example, a clinician may release valve clip 102, when in the extended configuration or a configuration between the extended configuration and the contracted configuration, such that valve clip 102 snaps back or rapidly and uncontrollably returns to the contracted configuration, e.g., to the extend allowed when engaging leaflets LF.

As valve clip 102 moves from the extended configuration to the contracted configuration, valve clip 102 may engage leaflets LF. For example, as illustrated in FIG. 2C, valve clip 102 may coil around the free edges of leaflets LF. By coiling around leaflets LF, valve clip 102 engages the tissue of leaflets LF. In some examples, engaging leaflets LF with valve clip 102 may be relatively easier than clamping leaflets LF individually. For example, valve clip 102 may be deployed and moved from the extended configuration to the contracted configuration without requiring precise positioning to capture free edges of leaflets LF (compared to individually clipping edges of leaflets LF).

In some examples, the design of valve clip 102 and delivery devices 110 may allow placement of valve clip 102 to be evaluated prior to releasing valve clip 102 from delivery devices 110. For example, a radio-fluorescent dye may be injected into the beating heart of the patient to observe coaptation after placement of valve clip 102. In some examples, valve clip 102 may be repositioned by manipulating control members 124 to move delivery devices 110 to return valve clip 102 toward the extended configuration, repositioning valve clip 102, and manipulating control members 124 to move delivery devices 110 to manipulate valve clip 102 toward the contracted configuration.

Figure 2D:
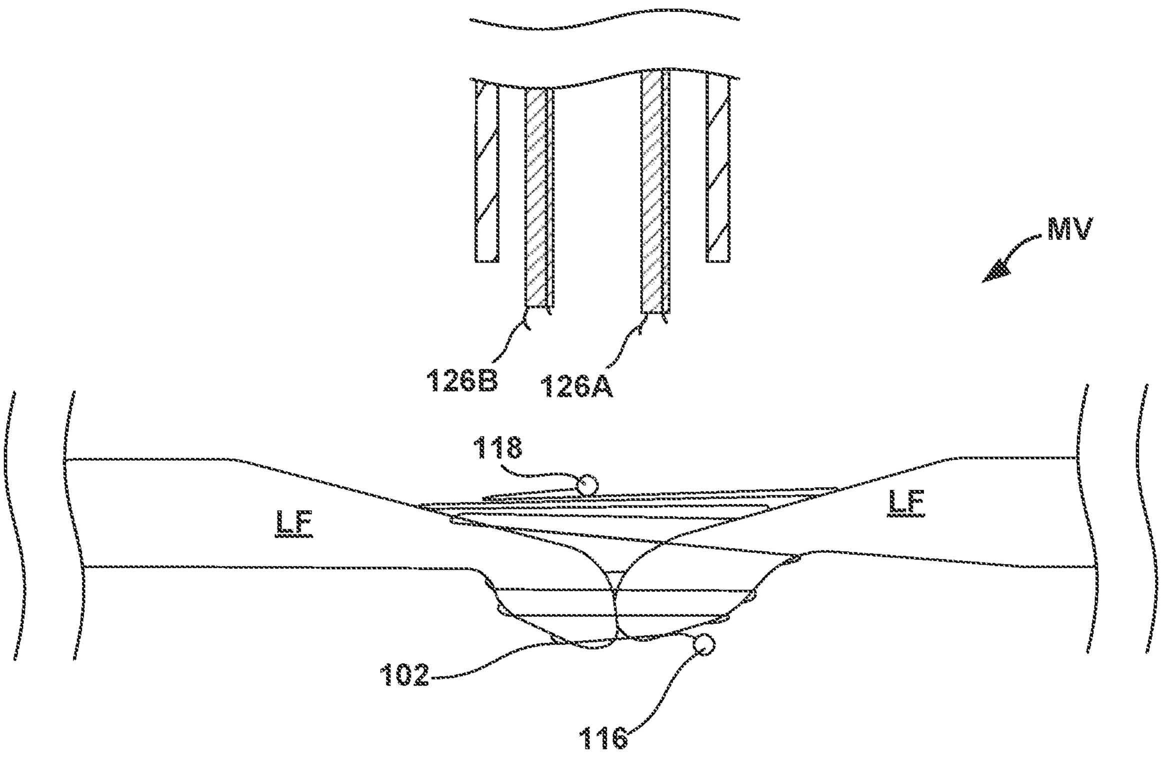

As illustrated in FIG. 2D, once valve clip 102 has substantially returned to the contracted configuration, a clinician may control one or both of control members 124 to control the corresponding delivery device(s) to release valve clip 102. When engaged with a selected tissue, valve clip 102 may be at least partially deformed such that valve clip 102 applies a force to the tissue to engage the tissue. In some examples, even after releasing valve clip 102, valve clip 102 may still be removable. For example, a clinician may control one or both of control members 124 to engage the corresponding delivery device(s) 110 with valve clip 102 to move valve clip 102 toward the extended configuration to retrieve valve clip 102. Retrieval of valve clip 102 may be beneficial when, for example, coaptation becomes unsatisfactory over time or a different means of treating valvular insufficiency or regurgitation is to be used at the valve.

Figure 3A:
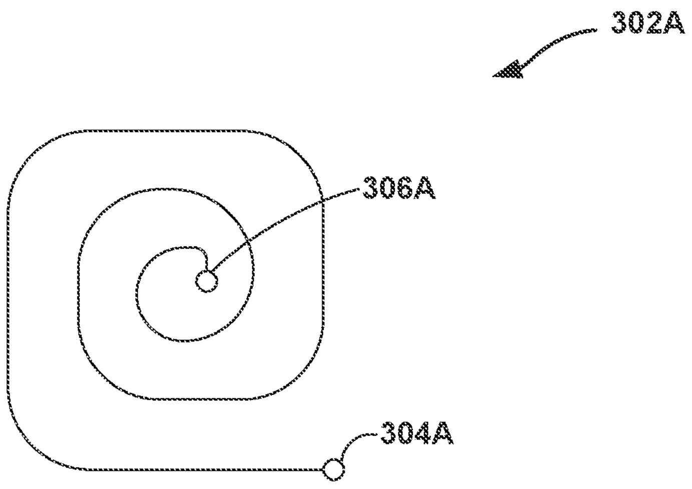
FIGS. 3A-3C are schematic diagrams illustrating plan views of example valve clips defining spiral shapes.
Figure 3B:
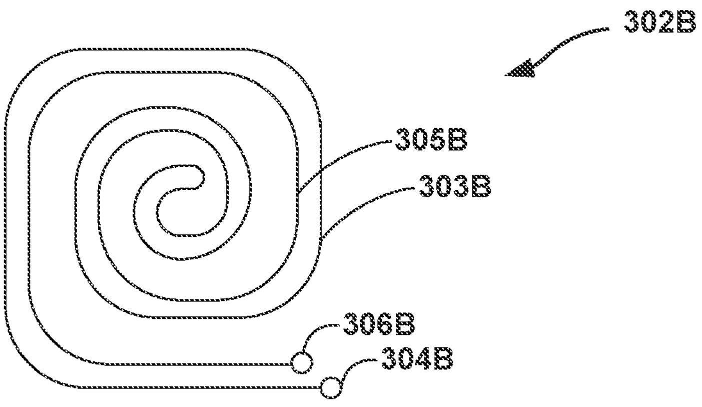
Figure 3C:
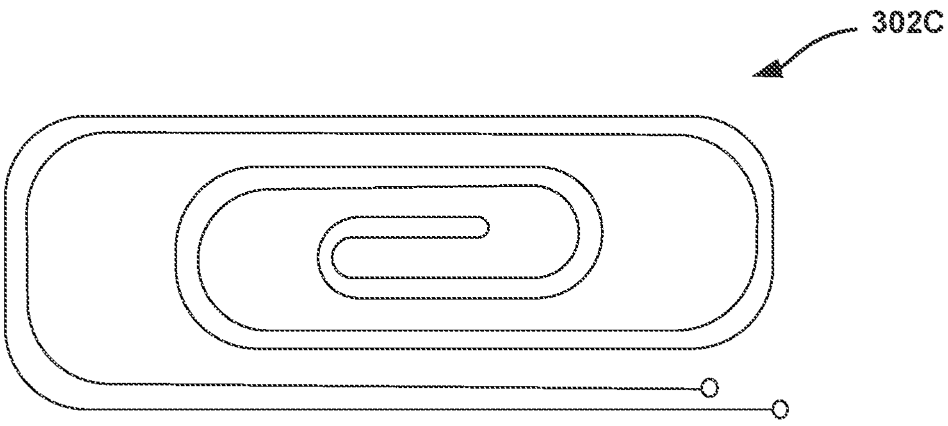

As discussed above, the preformed shape of a valve clip may include a substantially planar spiral (e.g., planar within manufacturing tolerances), non-planar spiral, a helix, or other spring-like shape. FIGS. 3A-3C are schematic diagrams illustrating plan views of example valve clips 302A, 302B, and 302C. As illustrated in FIG. 3A, valve clip 302A defines a spiral extending from a proximal end 304A to a distal end 306A. As illustrated in FIG. 3B, valve clip 302B defines a dual spiral extending from a proximal portion 303B including proximal end 304B to a distal portion 305B including distal end 306B. In some examples, a dual spiral may improve capstan effect by positioning proximal portion 303B and distal portion 305B on opposing sides of a valve when in the contracted configuration. Generally, the preformed shape may define any suitable shape. For example, as illustrated in FIG. 3C, valve clip 302C defines an elongate dual spiral.

Figure 4A:
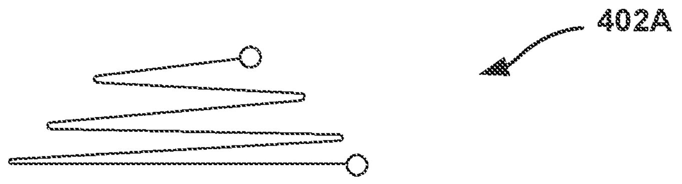
FIGS. 4A and 4B are schematic diagrams illustrating example valve clips having non-planar side profiles.
Figure 4B:
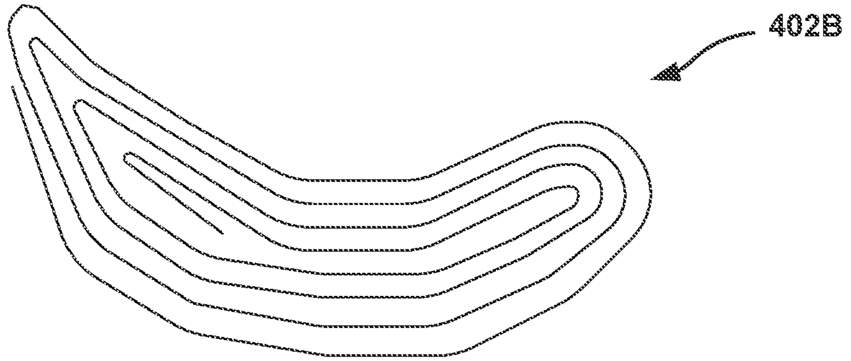

The preformed shape of a valve clip may be planar or non-planar. FIGS. 4A and 4B are schematic diagrams illustrating example valve clips 402A and 402B having non-planar side profiles. In some examples, a valve clip may be substantially planar within common manufacturing tolerances. As illustrated in the sideview of FIG. 4A, valve clip 402B defines a helix. Although illustrated as a single conical helix, in some examples, a valve clip may include a double helix or a non-conical helix. In some examples, the preformed shape of the valve clip may be selected to correspond to a shape of an anatomical surface. For example, as illustrated in the elevated view of FIG. 4B, the preformed shape of valve clip 402B may be selected to define a saddle shape, similar to the saddle shape of a native mitral valve.

Figure 5:
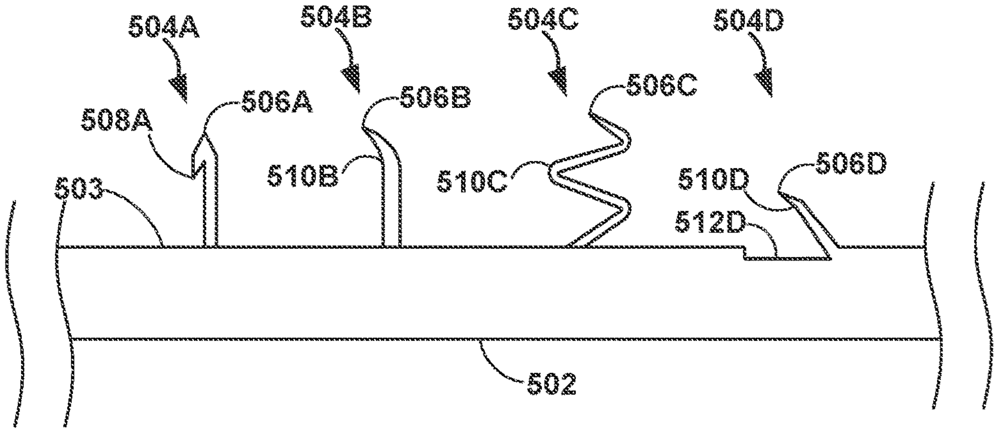
FIG. 5 is a schematic diagram illustrating example anchors extending from an exterior surface of a valve clip.

As discussed above in reference to FIGS. 2A-2D, valve clip 102 may optionally include at least one anchor. FIG. 5 is a schematic diagram illustrating example anchors 504A, 504B, 504C, and 504D ("anchors 504") extending from an exterior surface 503 of valve clip 502. Anchors 504 include structures configured to engage valve clip 502 to tissue at the selected tissue site, such as to leaflets LF, and help retain valve clip 502 substantially in place relative to the selected tissue site. For example, anchors 504 are configured to at least one of penetrate at least a portion of the tissue at the selected tissue site, increase a coefficient of friction (e.g., improve capstan effect) at the selected tissue site, and/or promote tissue ingrowth.

Anchor 504A includes a point 506A and barb 508A. Point 506A is configured to penetrate tissue, e.g., leaflets LF. After tissue penetration of a selected depth, barb 508A is configured to engage the tissue to retain valve clip 502 substantially in place. Anchor 504B includes a tine having a point 506B configured to penetrate tissue and a curved portion 510B configured to engage the tissue to retain valve clip 502 substantially in place. Anchor 504C includes a helical coil having a point 506C configured to penetrate tissue and a plurality of curved portions 510C configured to engage the tissue to retain valve clip 502 substantially in place. In some examples, the helical coil may include other helical shapes, such as a double helix or a conical helix. Anchor 504D includes a hook having a point 506D configured to penetrate tissue and a curved portion 510C configured to engage the tissue to retain valve clip 502 substantially in place. In some examples, anchor 504D may be formed by machining exterior surface 503 of valve clip 502. For example, exterior surface 503 may be laser ablated to at least partially metal a portion of exterior surface 503, forming a depression 512D and anchor 504D.

Figure 6:
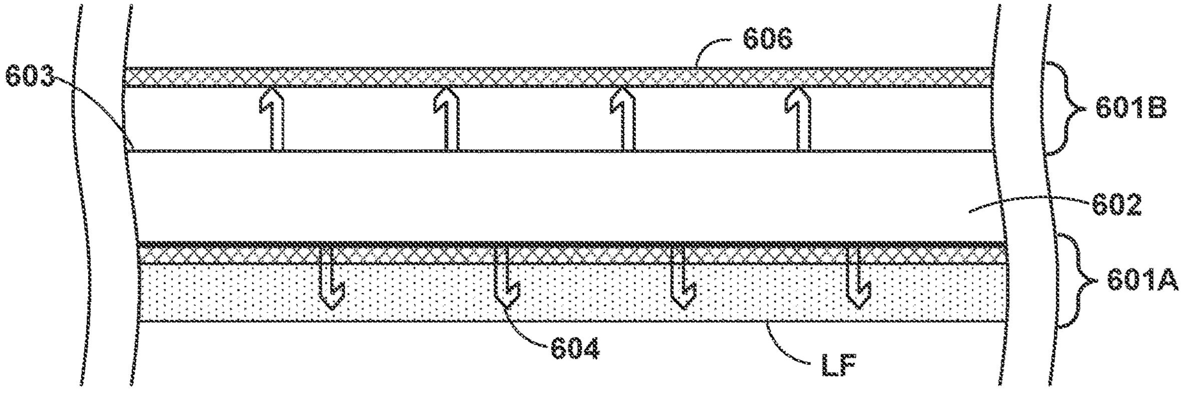
FIG. 6 is a schematic diagram illustrating an example valve clip that includes anchors and a fabric.

In some examples, the anchors may include a fabric. FIG. 6 is a schematic diagram illustrating an example valve clip 602 that includes anchors 604 and a fabric 606. In the example of FIG. 6, anchors 604 may extend around a perimeter of valve clip 602 defined by exterior surface 603. For example, a first side 601A of valve clip 602 may be positioned adjacent (e.g., contacting) tissue at a selected tissue site. A second side 601B of valve clip 602 may be positioned opposite the tissue-contacting side of valve clip 602. In some examples, prior to deployment of valve clip 602 from a delivery catheter (e.g., catheter 104), fabric 606 may be disposed external to anchors 604. During deployment, anchors 604 may penetrate fabric 606 and subsequently penetrate tissue at the selected tissue site. For example, a force applied to tissue by movement of valve clip 602 from the extended configuration to the contracted configuration may cause anchors 602 to penetrate fabric 606 and tissue 602. As illustrated in FIG. 6, anchors 604 on first side 601A (e.g., the tissue-contacting side) may penetrate fabric 606 and at least a portion of tissue, e.g., leaflet LF. Anchors 604 on second side 601B (e.g., opposite tissue-contacting side) may not penetrate fabric 606. In this way, fabric 606 may reduce interference between anchors 604 and the sidewall of the delivery catheter during deployment and/or anatomical surfaces that are not the selected tissue site.

Figure 7:
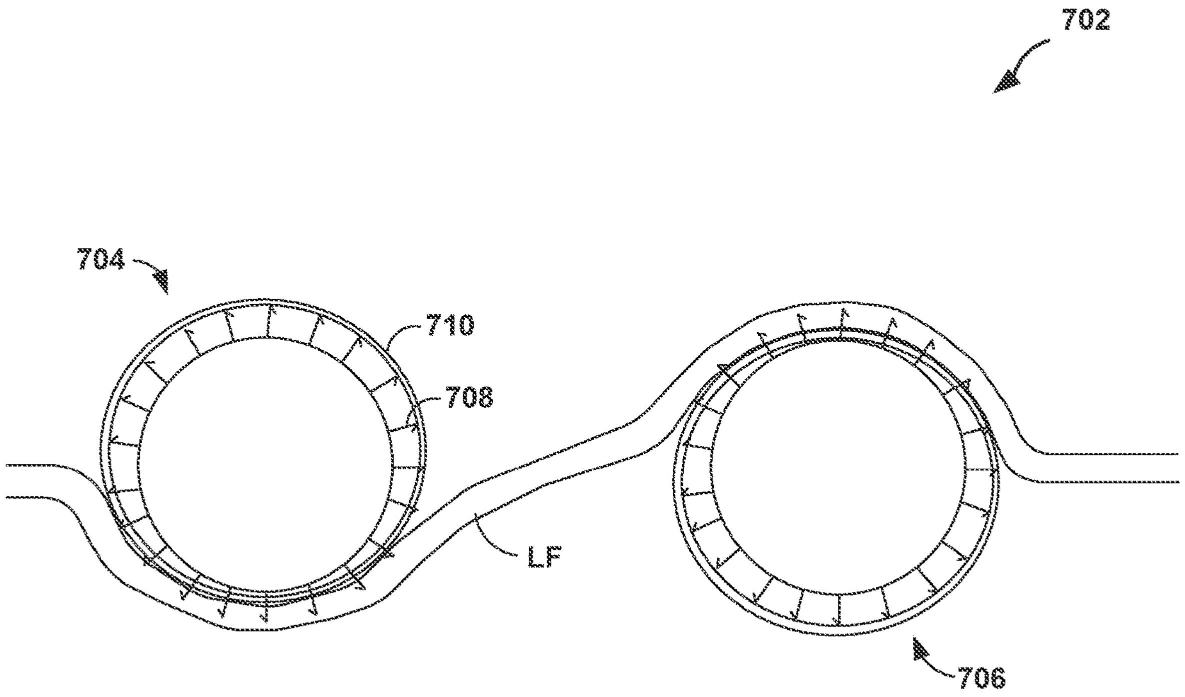
FIG. 7 is a schematic diagram illustrating a portion of an example valve clip engaged with tissue.

FIG. 7 is a schematic diagram illustrating a portion of an example valve clip 702 engaged with tissue. Valve clip 702 includes a first portion 704 extending on an atrial side of leaflet LF and a second portion 706 extending on a ventricular side of leaflet LF. Valve clip 702 includes a plurality of anchors 708 extending from an exterior surface of valve clip 702. Valve clip 702 also includes a fabric 710 extending over anchors 708. As discussed above with reference to FIG. 6, along the tissue contacting sides of valve clip 702, anchors 708 may penetrate fabric 710 and at least a portion of leaflet LF. Additionally, by alternating between the atrial side of leaflet LF and the ventricular side of leaflet LF, first portion 704 and second portion 706 may result in a capstan effect having a friction force, alone or together with anchors 708 and fabric 710, sufficient to retain valve clip 702 on leaflet LF.

Figure 8:
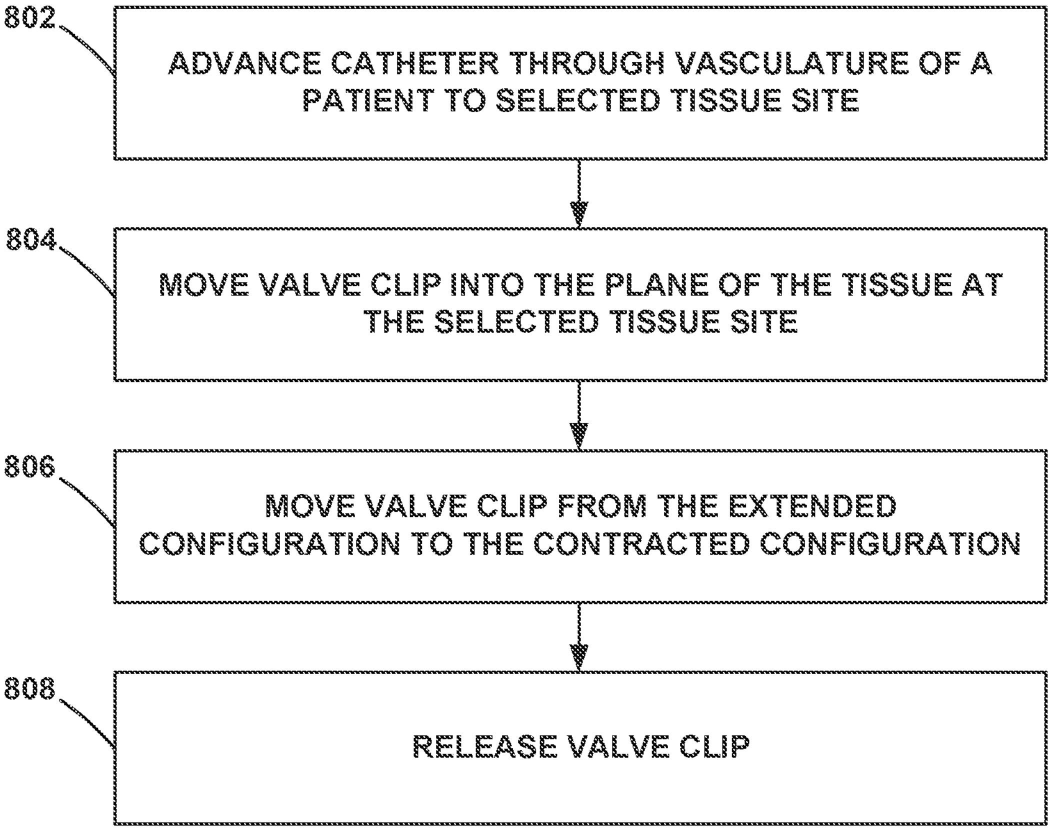
FIG. 8 is a flow diagram illustrating an example technique for introducing a valve clip.

FIG. 8 is a flow diagram illustrating an example technique for introducing a valve clip. The technique of FIG. 8 will be described with concurrent reference to valve clip 102 of FIGS. 2A-2D, although it will be understood that the technique of FIG. 8 may be used to introduce other valve clips described herein, and the valve clips described herein may be introduced using other techniques.

Distal portion 105 of catheter 104 may be advanced through vasculature of a patient to a selected tissue site (802). For example, a clinician may introduce distal portion 105 of catheter 104 into vasculature of a patient transcutaneously. For instance, distal portion 105 of catheter 104 may be introduced to a femoral or radial artery. Distal portion 105 of catheter 104 may be advanced through vasculature of the patient to the selected tissue site by a clinician manipulating handle 106 of distal portion 105 of catheter 104. In some examples, distal portion 105 of catheter 104 may include a steerable shaft or tip to allow the clinician to direct distal portion 105 of catheter 104 through bends, curves, and branching points of the vasculature.

In some examples, the selected tissue site may include the mitral valve MV, and distal portion 105 of catheter 104 may be advanced to the left atrium LA. In other examples, the selected tissue site may include another heart valve. In other examples, the selected tissue site may include other vasculature valves or other anatomical tissue that may be joined using the valve clips described herein. Distal portion 105 of catheter 104 may access the left atrium trans-septally, trans-aortically, or trans-apically. In some examples, distal portion 105 of catheter 104 may be tracked over a guide wire, through a guide catheter, or the like as distal portion 105 of catheter 104 is advanced to the selected tissue site. Distal portion 105 of catheter 104 may include one or more radiological markers at or near a distal end of distal portion 105 of catheter 104 to assist visualizing distal portion 105 of catheter 104 as it is advanced to the selected tissue site.

Once distal portion 105 of catheter 104 (e.g., distal opening 112) has been advance to the selected tissue site, delivery devices 110 may be manipulated to move valve clip 102 in the extended configuration distal to distal opening 112 (804). For example, a clinician may control delivery device 110 to move valve clip 102 into the plane of the mitral valve MV.

After positioning valve clip 102 in the extended configuration, delivery devices 110 may be manipulated to move valve clip 102 from the extended configuration to the contracted configuration to engage tissue at the selected tissue site (806). In some examples, the placement of valve clip 102, when engaged with the tissue, may be evaluated. For example, a radio-fluorescent dye may be injected into the left atrium LA and/or left ventricle LV to evaluate coaptation of the mitral valve. After moving valve clip 102 to the contracted configuration, delivery devices 110 may be controlled to release valve clip 102 (808).

The following clauses illustrate example subject matter described herein.

Clause 1. A medical system comprising: a valve clip comprising a deformable wire configured to engage valve leaflets of a patient, wherein the deformable wire extends from a first wire portion to a second wire portion; and a catheter configured to introduce the valve clip adjacent a native heart valve in a patient, the catheter comprising: a handle comprising a plurality of control members; an elongate body defining a lumen, wherein the elongate body extends from a proximal end mechanically coupled to the handle to a distal portion comprising a distal opening; a first delivery device operatively coupled to at least one control member of the plurality of control members and extending through the lumen to the distal opening, wherein the first delivery device is configured to be releasably coupled to the first wire portion and moveable relative to the distal opening of the elongate body; and a second delivery device operatively coupled to at least one control member of the plurality of control members and extending through the lumen to the distal opening, wherein the second delivery device is configured to be releasably coupled to the second wire portion, wherein the first and second delivery device are configured to move the valve clip between an extended configuration and a contracted configuration to engage the valve leaflets.

Clause 2. The medical system of clause 1, wherein the valve clip, when in the extended configuration, is configured to pass through the lumen and the distal opening of the elongate body, and wherein the valve clip, when in the contracted configuration, defines a preformed shape configured to engage the valve leaflets.

Clause 3. The medical system of clause 1 or 2, wherein the first wire portion is a distal portion of the deformable wire, wherein the second wire portion is a proximal portion of the deformable wire, wherein at least one of the proximal end or the distal end comprises a fixation structure, and wherein at least one of the first or second delivery devices is configured to releasably couple to the fixation structure.

Clause 4. The medical system of any one of clauses 1 to 3, wherein the deformable wire comprises at least one of a biocompatible shape memory alloy or a nickel-titanium alloy.

Clause 5. The medical system of any one of clauses 1 to 4, wherein the valve clip comprises at least one anchor extending from an exterior surface of the deformable wire and configured to engage the valve leaflets.

Clause 6. The medical system of clause 5, wherein the at least one anchor comprises a fabric, one or more barbs, one or more hooks, one or more helical coils, or one or more conical helical coils.

Clause 7. The medical system of clause 5 or 6, wherein the at least one anchor comprises at least one of a biocompatible shape memory alloy or a nickel-titanium alloy.

Clause 8. The medical system of any one of clauses 1 to 7, wherein the valve clip comprises a plurality of barbs extending from an exterior of the deformable wire and a fabric positioned over the plurality of barbs, wherein the barbs are configured to at least partially protrude through the fabric when the valve clip engages the valve leaflets.

Clause 9. The medical system of any one of clauses 1 to 8, wherein the valve leaflets comprise leaflets of a mitral valve of a heart.

Clause 10. A medical system comprising: a valve clip comprising: a deformable wire extending from a distal fixation structure to a proximal fixation structure, wherein the deformable wire is moveable between an extended configuration and a preformed contracted configuration configured to engage valve leaflets; a plurality of barbs extending from an exterior surface of the wire; and a fabric positioned exterior to the plurality of barbs, wherein the plurality of barbs are configured to at least partially protrude through the fabric when the wire engages the valve leaflets; and a catheter configured to introduce the valve clip adjacent a native heart valve in a patient, the catheter comprising: a handle comprising a plurality of control members; an elongate body defining a lumen, wherein the elongate body extends from a proximal end mechanically coupled to the handle to a distal opening; a first delivery device operatively coupled to at least one control member of the plurality of control members and extending through the lumen to the distal opening, wherein the first delivery device is configured to be releasably coupled to the distal fixation member of the deformable wire and movable relative to the distal opening of the elongate body; and a second delivery device of the plurality of delivery devices operatively coupled to at least one control member of the plurality of control members and extending through the lumen to the distal opening, wherein the second delivery device is configured to be releasably coupled to the proximal fixation member of the deformable wire, wherein the first and second delivery device are configured to pass the valve clip in the extended configuration through the distal opening of the elongate body and move the valve clip between the extended configuration and the contracted configuration to engage the valve leaflets.

Clause 11. The medical system of clause 10, wherein the deformable wire comprises at least one of a biocompatible shape memory alloy or a nickel-titanium alloy.

Clause 12. The medical system of clause 10 or 11, wherein the valve leaflets comprises leaflets of a mitral valve of a heart.

Clause 13. A method comprising: advancing a catheter through vasculature of a patient to a vascular or cardiac selected tissue site, wherein the catheter comprises a lumen housing a valve clip comprising a deformable wire configured to engage valve leaflets of a patient, wherein the deformable wire extends from a first wire portion to a second wire portion, and wherein the catheter further comprises: a handle comprising a plurality of control members; an elongate body defining the lumen, wherein the elongate body extends from a proximal end mechanically coupled to the handle to a distal portion comprising a distal opening; and a first delivery device operatively coupled to at least one control member of the plurality of control members and extending through the lumen to the distal opening, wherein the first delivery device is configured to be releasably coupled to the first wire portion and movable relative to the distal opening of the elongate body; and a second delivery device of the plurality of delivery devices operatively coupled to at least one control member of the plurality of control members and extending through the lumen to the distal opening, wherein the second delivery device is configured to be releasably coupled to the second wire portion; advancing the first delivery device distal to the distal opening of the elongate body; and controlling the first delivery device and the second delivery device to move the valve clip from an extended configuration to a contracted configuration to engage the valve leaflets.

Clause 14. The method of clause 13, wherein the valve clip, when in the extended configuration, is configured to pass through the lumen and the distal opening of the elongate body, and wherein the valve clip, when in the contracted configuration, defines a preformed shape configured to engage the valve leaflets.

Clause 15. The method of clause 13 or 14, wherein the first wire portion is a distal portion of the deformable wire, wherein the second wire portion is a proximal portion of the deformable wire, and wherein at least one of the proximal end or the distal end comprises a fixation structure, the method further comprising coupling at least one of the first or second delivery devices to the fixation structure.

Clause 16. The method of any one of clauses 13 to 15, wherein the deformable wire comprises at least one of a biocompatible shape memory alloy or a nickel-titanium alloy.

Clause 17. The method of any one of clauses 13 to 16, wherein the valve clip comprises at least one anchor extending from an exterior surface of the deformable wire, and wherein moving the valve clip from an extended configuration to a contracted configuration comprises engaging the at least one anchor with the valve leaflets.

Clause 18. The method of clause 17, wherein the at least one anchor comprises a fabric, one or more barbs, one or more hooks, one or more helical coils, or one or more conical helical coils.

Clause 19. The method of any one of clauses 13 to 18, wherein the valve clip comprises a plurality of barbs extending from an exterior of the deformable wire and a fabric positioned over the plurality of barbs, wherein the barbs are configured to at least partially protrude through the fabric when the valve clip engages the valve leaflets.

Clause 20. The method of any one of clauses 13 to 19, wherein the valve leaflets comprise leaflets of a mitral valve of a heart, and wherein advancing the catheter through vasculature of a patient to a vascular or cardiac selected tissue site comprises: advancing the catheter through the vasculature of the patient to a right atrium of the patient; and advancing the catheter through a septum of the heart to the left atrium.

Various examples have been described. Any combination of the described systems, devices, operations, or functions is contemplated. These and other examples are within the scope of the following claims.

What is claimed is:

1. A medical system comprising:

a valve clip comprising a deformable wire configured to capture two or more valve leaflets of a patient, wherein the deformable wire extends from a first wire portion to a second wire portion; and a catheter configured to introduce the valve clip adjacent a native heart valve in a patient, the catheter comprising:

a handle comprising a plurality of control members;

an elongate body defining a lumen, wherein the elongate body extends from a proximal end mechanically coupled to the handle to a distal end comprising a distal opening;

a first delivery device operatively coupled to at least one control member of the plurality of control members and extending through the lumen to the distal opening, wherein the first delivery device is configured to be releasably coupled to the first wire portion and moveable relative to the distal opening of the elongate body; and a second delivery device operatively coupled to at least one control member of the plurality of control members and extending through the lumen to the distal opening, wherein the second delivery device is configured to be releasably coupled to the second wire portion, wherein the first and second delivery devices are configured to move the valve clip between an extended configuration and a contracted configuration to capture the two or more valve leaflets.

2. The medical system of claim 1, wherein the valve clip, when in the extended configuration, is configured to pass through the lumen and the distal opening of the elongate body, and wherein the valve clip, when in the contracted configuration, defines a preformed shape configured to capture the two or more valve leaflets.

3. The medical system of claim 1, wherein the first wire portion is a distal portion of the deformable wire, wherein the second wire portion is a proximal portion of the deformable wire, wherein at least one of the proximal end or the distal end comprises a fixation structure, and wherein at least one of the first or second delivery devices is configured to releasably couple to the fixation structure.

4. The medical system of claim 1, wherein the deformable wire comprises at least one of a biocompatible shape memory alloy or a nickel-titanium alloy.

5. The medical system of claim 1, wherein the valve clip comprises at least one anchor extending from an exterior surface of the deformable wire and configured to capture the two or more valve leaflets.

6. The medical system of claim 5, wherein the at least one anchor comprises a fabric, one or more barbs, one or more hooks, one or more helical coils, or one or more conical helical coils.

7. The medical system of claim 6, wherein the at least one anchor comprises at least one of a biocompatible shape memory alloy or a nickel-titanium alloy.

8. The medical system of claim 1, wherein the valve clip comprises a plurality of barbs extending from an exterior of the deformable wire and a fabric positioned over the plurality of barbs, wherein the barbs are configured to at least partially protrude through the fabric when the valve clip captures the two or more valve leaflets.

9. The medical system of claim 1, wherein the contracted configuration of the valve clip defines a preformed shape to which the valve clip recovers in the absence of an applied force, and wherein, to capture the two or more valve leaflets, the deformable wire is configured to grasp the two or more valve leaflets when the valve clip is in the contracted configuration to clip together the two or more valve leaflets.

10. The medical system of claim 1, wherein the first and second delivery devices are non-coaxial.

11. A medical system comprising:

a valve clip comprising:

a deformable wire extending from a distal fixation structure to a proximal fixation structure, wherein the deformable wire is moveable between an extended configuration and a preformed contracted configuration configured to capture two or more valve leaflets;

a plurality of barbs extending from an exterior surface of the wire; and a fabric positioned exterior to the plurality of barbs, wherein the plurality of barbs are configured to at least partially protrude through the fabric when the wire captures the two or more valve leaflets; and a catheter configured to introduce the valve clip adjacent a native heart valve in a patient, the catheter comprising:

a handle comprising a plurality of control members;

an elongate body defining a lumen, wherein the elongate body extends from a proximal end mechanically coupled to the handle to a distal end comprising a distal opening;

a first delivery device operatively coupled to at least one control member of the plurality of control members and extending through the lumen to the distal opening, wherein the first delivery device is configured to be releasably coupled to the distal fixation structure of the deformable wire and movable relative to the distal opening of the elongate body; and a second delivery device operatively coupled to at least one control member of the plurality of control members and extending through the lumen to the distal opening, wherein the second delivery device is configured to be releasably coupled to the proximal fixation structure of the deformable wire, wherein the first and second delivery devices are configured to pass the valve clip in the extended configuration through the distal opening of the elongate body and move the valve clip between the extended configuration and the contracted configuration to capture the two or more valve leaflets.

12. The medical system of claim 11, wherein the deformable wire comprises at least one of a biocompatible shape memory alloy or a nickel-titanium alloy.

13. A method comprising:

advancing a catheter through vasculature of a patient to a vascular or cardiac selected tissue site, wherein the catheter comprises a lumen housing a valve clip comprising a deformable wire configured to capture two or more valve leaflets of a patient, wherein the deformable wire extends from a first wire portion to a second wire portion, and wherein the catheter further comprises:

a handle comprising a plurality of control members;

an elongate body defining the lumen, wherein the elongate body extends from a proximal end mechanically coupled to the handle to a distal end comprising a distal opening; and a first delivery device operatively coupled to at least one control member of the plurality of control members and extending through the lumen to the distal opening, wherein the first delivery device is configured to be releasably coupled to the first wire portion and movable relative to the distal opening of the elongate body; and a second delivery device operatively coupled to at least one control member of the plurality of control members and extending through the lumen to the distal opening, wherein the second delivery device is configured to be releasably coupled to the second wire portion;

advancing the first delivery device distal to the distal opening of the elongate body; and controlling the first delivery device and the second delivery device to move the valve clip from an extended configuration to a contracted configuration to capture the two or more valve leaflets.

14. The method of claim 13, wherein the valve clip, when in the extended configuration, is configured to pass through the lumen and the distal opening of the elongate body, and wherein the valve clip, when in the contracted configuration, defines a preformed shape configured to capture the two or more valve leaflets.

15. The method of claim 13, wherein the first wire portion is a distal portion of the deformable wire, wherein the second wire portion is a proximal portion of the deformable wire, and wherein at least one of the proximal end or the distal end comprises a fixation structure, the method further comprising coupling at least one of the first or second delivery devices to the fixation structure.

16. The method of claim 13, wherein the deformable wire comprises at least one of a biocompatible shape memory alloy or a nickel-titanium alloy.

17. The method of claim 13, wherein the valve clip comprises at least one anchor extending from an exterior surface of the deformable wire, and wherein moving the valve clip from the extended configuration to the contracted configuration comprises engaging the at least one anchor with the two or more valve leaflets.

18. The method of claim 17, wherein the at least one anchor comprises a fabric, one or more barbs, one or more hooks, one or more helical coils, or one or more conical helical coils.

19. The method of claim 13, wherein the valve clip comprises a plurality of barbs extending from an exterior of the deformable wire and a fabric positioned over the plurality of barbs, wherein the barbs are configured to at least partially protrude through the fabric when the valve clip captures the two or more valve leaflets.

20. The method of claim 13, wherein the two or more valve leaflets comprise leaflets of a mitral valve of a heart, and wherein advancing the catheter through vasculature of a patient to a vascular or cardiac selected tissue site comprises:

advancing the catheter through the vasculature of the patient to a right atrium of the patient; and advancing the catheter through a septum of the heart to a left atrium.

* * * * *